United States Patent
Williams et al.

[11] Patent Number: 5,887,716
[45] Date of Patent: Mar. 30, 1999

[54] LIQUID STERILANT CASSETTE AND INDICIA SYSTEM

[75] Inventors: Hal Williams, San Clemente; Robert Spencer; Alfredo Choperena, both of San Juan Capistrano, all of Calif.

[73] Assignee: Johnson & Johnson Medical, Inc., Arlington, Tex.

[21] Appl. No.: 869,869

[22] Filed: Jun. 2, 1997

[51] Int. Cl.⁶ .................................................. B65D 85/00
[52] U.S. Cl. ............................ 206/459.1; 40/312; 141/1; 235/487
[58] Field of Search ................................. 206/499.1, 484, 206/387.1; 221/2, 7; 235/487; 40/312; 141/1, 141; D24/9

[56] References Cited

U.S. PATENT DOCUMENTS

| | | | |
|---|---|---|---|
| D. 306,065 | 2/1990 | Williams et al. | D24/9 |
| D. 306,066 | 2/1990 | Williams et al. | D24/9 |
| D. 307,794 | 5/1990 | Williams et al. | D24/9 |
| 3,756,384 | 9/1973 | Stone | 40/312 X |
| 4,643,876 | 2/1987 | Jacobs et al. | |
| 4,817,800 | 4/1989 | Williams et al. | 206/484 |
| 4,869,286 | 9/1989 | Williams et al. | |
| 4,899,519 | 2/1990 | Williams et al. | 53/449 |
| 4,913,196 | 4/1990 | Williams et al. | 141/1 |
| 4,938,262 | 7/1990 | Williams et al. | 141/114 |
| 4,941,518 | 7/1990 | Williams et al. | 191/1 |
| 5,016,262 | 5/1991 | Cushing | 206/459.1 X |
| 5,691,530 | 11/1997 | Solitt | 235/487 |

FOREIGN PATENT DOCUMENTS

950173  2/1964  United Kingdom ............ 2069 459.1

*Primary Examiner*—Bryon P. Gehman
*Attorney, Agent, or Firm*—Andrew C. Farmer

[57] ABSTRACT

A method for delivering liquids is disclosed wherein a quantity of the liquid is provided within a cell within a cassette. The cassette is received within a sleeve having an open end. A flap at the open end of the sleeve extends inwardly through the open end between the sleeve and cassette to abut a lip on the cassette and hold the cassette therein. Impingement of the flap pushes the flap away from the lip to allow the cassette to move out of the sleeve. A label mounted within the sleeve rotates between a viewable position where it is visible through a window in the sleeve and a retracted position away from the window. Extraction and reinsertion of the cassette into the sleeve moves the label from the viewable to the nonviewable position.

22 Claims, 14 Drawing Sheets

LIQUID STERILANT CASSETTE AND INDICIA SYSTEM

FIELD OF THE INVENTION

The present invention relates to a system for storing and delivering cassettes to a device, and in an important embodient to the storage and delivery of cassettes containing liquid sterility to a sterilizing device.

BACKGROUND OF THE INVENTION

U.S. Pat. No. 4,643,876, incorporated herein by reference, discloses a sterilization system in which an agent such a hydrogen peroxide is introduced into a evacuated sterilizing chamber where it is vaporized and allowed to disperse onto the items to be sterilized. After a desired period of time, electrical energy is applied to the chamber to ionize the gas and form a plasma field at a power level sufficient to achieve sterilization.

This system has been successfully commercialized as the STERRAD® Sterilization system and is available from Advance Sterilization Products, Division of Ethicon, Inc., Irvine, Calif. The system is used in hospitals and other environments where it is operated repeatedly throughout the day by personnel having a widely varying range of understanding of the apparatus. To ensure simple and automatic operation with adequate safeguards with respect to human error, the system employs an automated delivery system for delivering the liquid sterility to the sterilization chamber. Measured portions of the sterility, in this case hydrogen peroxide but many other sterilizing agents could be substituted therefor, are provided in rupturable cells within a rigid cassette housing. A transport system maneuvers the cassette within the Sterrad® sterilizer and releases the given quantity of hydrogen peroxide into the sterilin chamber automatically. The cassette and operation of the deliver system are more fully described in the Williams et al, U.S. Pat. Nos. 4,817,800 issued Apr. 4, 1989; 4,913,196 issued Apr. 3, 1990; 4,938,262 issued Jul. 3, 1990; and 4,941,518 issued Jul. 17, 1990, all of which are incorporated herein by reference In this system, the operator manually grasps the cassette housing and inserts it into the sterilizer. When spent, the cassette is ejected and manually handled by the operator.

This sterilization device with the cassette system offers many advantages. The hydrogen peroxide and plasma kill a wide spectrum of bacteria, viruses, and spores at low temperatures which leave delicate temperature sensitive instruments undamaged. Hydrogen peroxide plasma sterilization meets several environmental and operator safety challenges. After the electromagnetic field producing the plasma is removed, the ionized plasma components recombine to form harmless water and oxygen, avoiding toxic disposal of the sterility used in the sterilization process. Also, the cassette effectively isolates the operator from the hydrogen peroxide contained therein.

One potential hazard arises from small drops of residual hydrogen peroxide which may be left on the exterior of a spent cassette. A sharp hollow needle pierces the cell which is then pressurized to extract the hydrogen peroxide solution through the needle. In some instances, it is possible for a drop of the solution to escape around the needle and thus remain on the cassette exterior after the extraction process. If an operator's skin or clothing were to contact this droplet, damage could result thereto. Also, operators have been known to accidentally insert a spent cassette into the sterilizer in the mistaken belief that it was actually a new cassette filled with sterility. Safety mechanisms in the process such as methods for detecting the presence of sterility during the sterilization cycle and biological indicators assessing the sterilization cycle efficiency. warn operators of potential cycle failures to prevent inadvertent use of non-sterile instruments thereafter. However, failure of a cycle due to use of a spent cassette entails delays and concomitant expenses.

The present cassette and delivery system encase the cassette within a protective sleeve which isolates the cassette from the operator's hands during all aspects of the cassette handling, thus protecting the operator from contact with any of the sterility contained therein. Further, an indicator on the sleeve, preferably a moveable label, indicates when the cassette has been used to prevent inadvertent re-use of a spent cassette.

SUMMARY OF THE INVENTION

A cassette assembly according to the present invention comprises a cassette having a first side and a first end and a protective sleeve containing the cassette. The sleeve comprises a first side and a first end, the first side having a window aperture therethrough. A label member within the sleeve has indicia thereon and is rotatably mounted about a first hinge adjacent the window aperture. The label moves between at least two position. In a first position of rotation about the first hinge, with the cassette within the sleeve, the label indicia is in registry with the window aperture and is visible therethrough. In a second position of rotation about the first hinge, with the cassette within the sleeve, the label indicia is out of registry with the window and indicia is not visible through the window aperture. The first hinge is oriented with respect to the sleeve first end so that when the cassette is inserted through the first end, the cassette abuts the label member and urges it about the hinge into the second position. Thus, extraction of the cassette from the sleeve and reinsertion of the cassette into the sleeve moves the label member from the first position to the second position to indicate that the cassette has been at least once extracted from the sleeve.

Preferably, the label member further comprises a biasing means to bias the label away from the first position when the cassette is not received within the sleeve. The biasing means can comprises an elastic member which urges the label member away from the first position, the label member having a mass and the sleeve being oriented so that gravity urges the mass of the label member away from the first position, a combination of the two, or other appropriate biasing.

Preferably, the label comprises an adhesive label adhered to the sleeve adjacent the window aperture and the first hinge comprises a fold line on the adhesive label. The sleeve can be formed of stock and further comprise a cut-out adjacent the viewing window which forms a removable panel of the stock, the adhesive label being attached thereto whereby the panel stiffens the label and defines the fold line thereon.

A retaining member, connected to the sleeve by a second hinge at the sleeve first end, can be provided to hold the cassette within the sleeve for easy removal. The retaining member rotates about the second hinge from a first position in which the retaining member blocks the travel of the cassette out of the sleeve through the sleeve first end and a second position in which the retaining member does not block travel of the cassette out of the sleeve through the sleeve first end. Preferably, the sleeve is formed of foldable stock, the retaining member comprises a flap, the second hinge comprises a first fold line in the stock and the biasing means comprises the tendency for the stock to unfold along the first fold line in the stock. The retaining member preferably extends from the second hinge, between the sleeve and the cassette, to a terminal edge which abuts a surface on the cassette when the retaining member is in its first position to block travel of the cassette out of the sleeve through the sleeve first end.

A method for delivering a cassette to a device according to the present invention comprises the steps of placing the cassette within a protective sleeve having an open end, hingably mounting a label member with an indicia thereon within the sleeve, rotating the label member into a first position with the indicia visible through a window aperture through the sleeve, abutting the label member with the cassette when the cassette is within the sleeve to hold the label member in the first position, sliding the cassette out of the sleeve through its open end; processing the cassette in the device; and sliding the cassette back into the sleeve through its open end and abutting the label member thereby to swing the label member to a second position with the indicia out of register with the window aperture and not visible therethrough.

The step of processing the cassette can comprise removing a substance from the cassette. The steps of sliding the cassette out of and back into the sleeve through its open end are preferably performed by a machine. The label indicia is preferably read with a sensor prior to the step of processing the cassette in the device. An automatic control unit can control these steps and is preferably programmed to not perform the steps of processing the cassette if the sensor fails to first read the presence of the label indicia, or if the indicia indicates something improper about the cassette. For instance, if the cassette is out of date, or contains the wrong type of material, or the wrong quantity, it can be rejected.

DETAILED DESCRIPTION OF THE INVENTION

Figure 1:
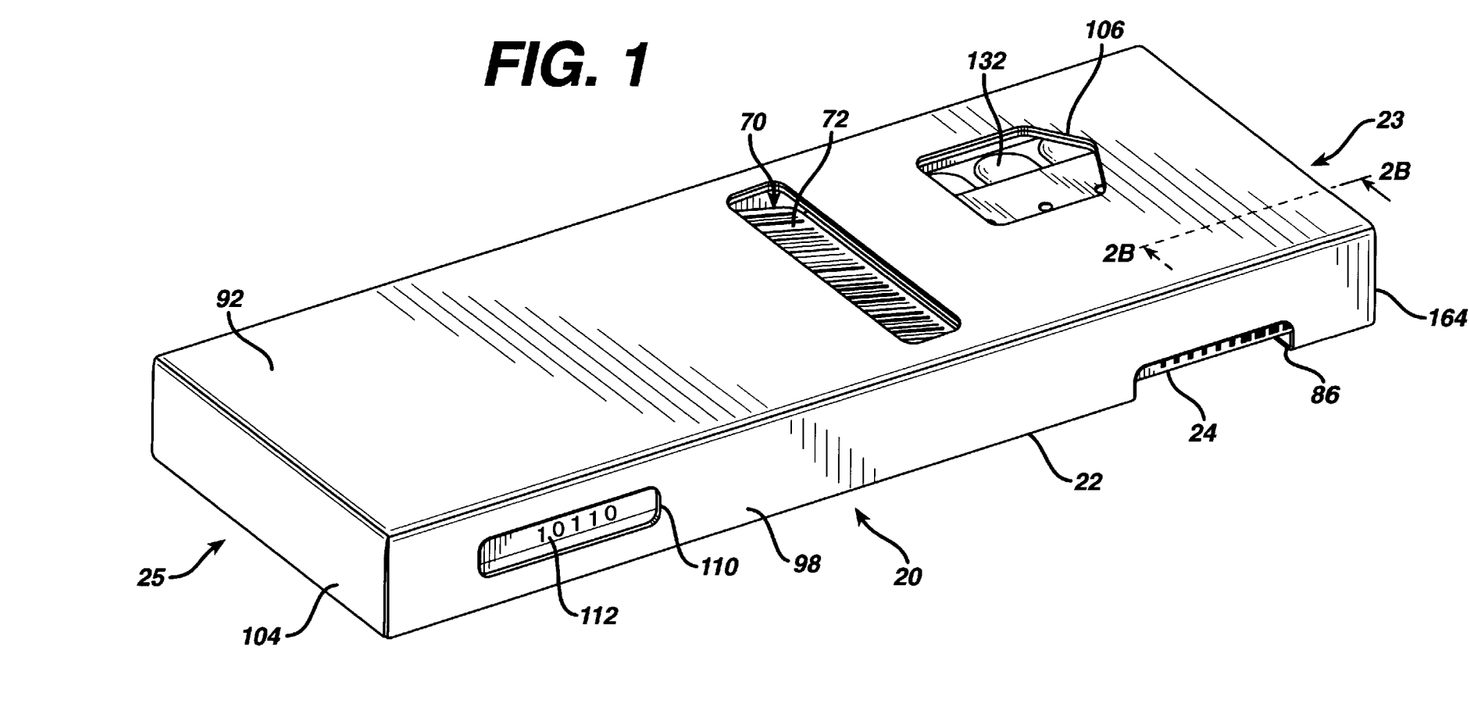
FIG. 1 is a perspective view of a cassette within a sleeve in accordance with the present invention.
Figure 2:
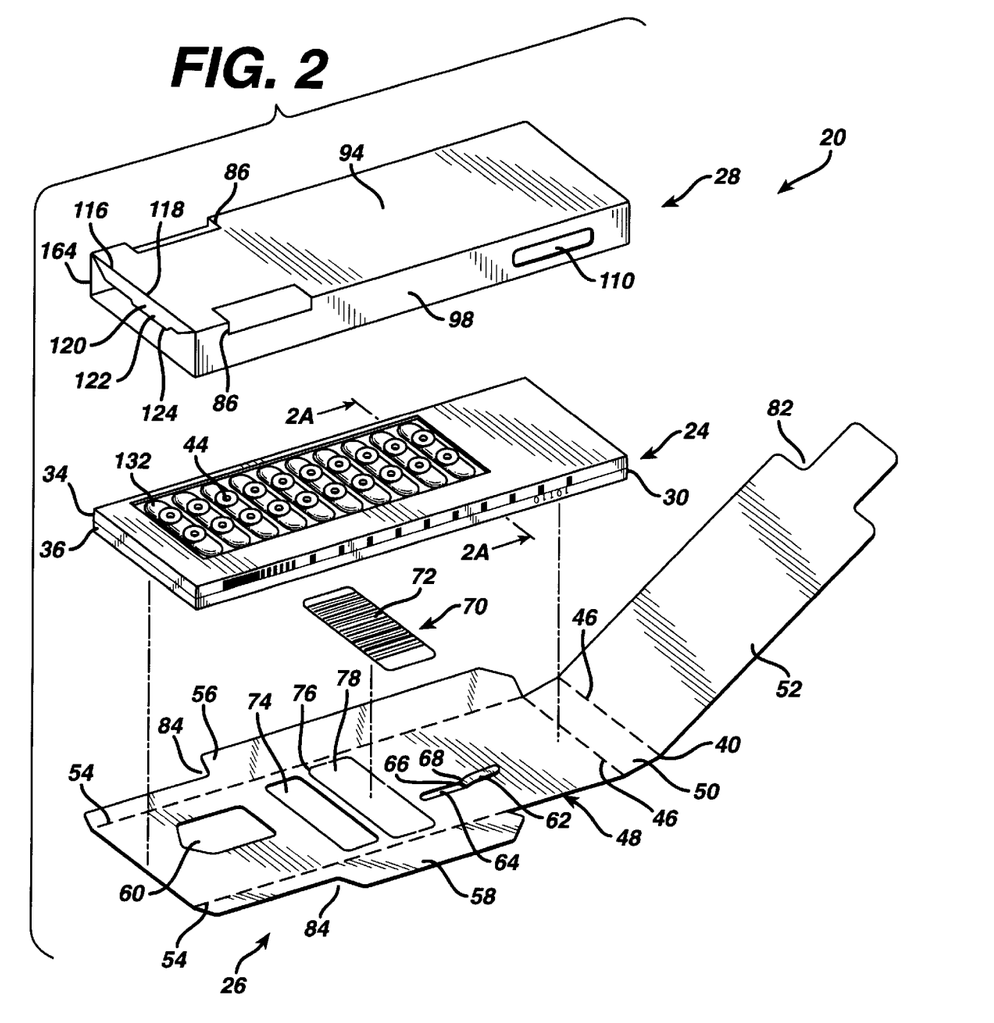
FIG. 2 is an exploded view of the cassette and sleeve of FIG. 1.
Figure 2A:
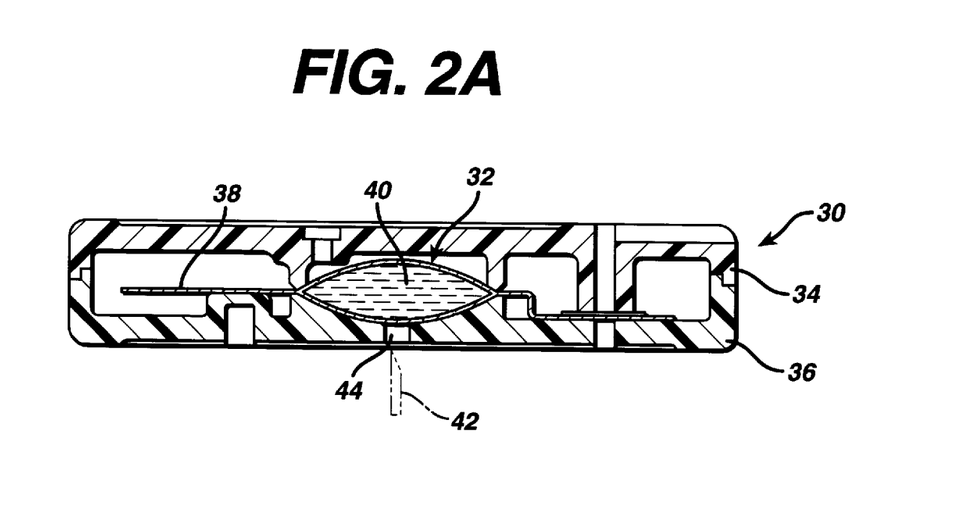
FIG. 2A is a view taken along line 2A—2A of FIG. 2.
Figure 2B:
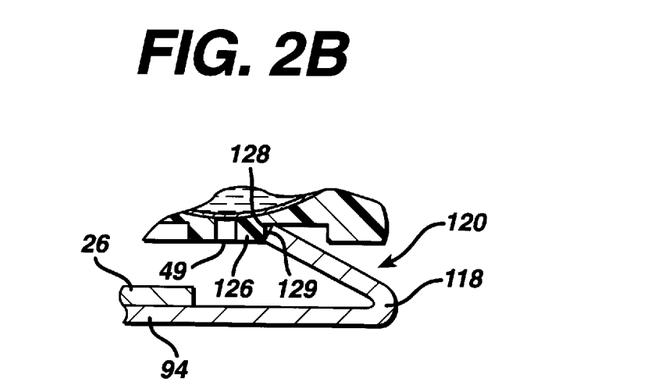
FIG. 2B is a sectional view taken along line 2B—2B of FIG. 1.

FIG. 1 illustrates an assembled cassette assembly 20 comprising a sleeve 22 containing a cassette 24 and the exploded view of FIG. 2 illustrates the components of the cassette assembly 20 in more detail. The sleeve 22 has an open end 23 and a closed end 25 and comprises an inner layer 26 of corrugated cardboard and an outer layer 28 of an attractive pressboard material. The cassette 24 comprises an elongated, rectangular plastic shell 30 containing a plurality of cells 32 containing a 58% solution of hydrogen peroxide. As seen in FIG. 2a, the cassette shell 30 is formed of an upper housing section 34 which mates with a lower housing section 36 to capture and to enclose a cell strip 38. The cell strip 38 is formed of a flexible material and contains the cells 32. Each cell 32 contains a precisely measured amount of hydrogen peroxide 40. Of course, other liquid sterilants may be substituted therefor. Preferably, the cassette shell 30 and cell strip 38 are formed of suitable polymers such as polystyrene and polyethylene, respectively. However, one of skill in the art will recognize that other materials may be substituted therefor. Each of the cells 32 is accessible by a hollow needle 42 through an aperture 44 in the cassette shell 30.

Figure 3:
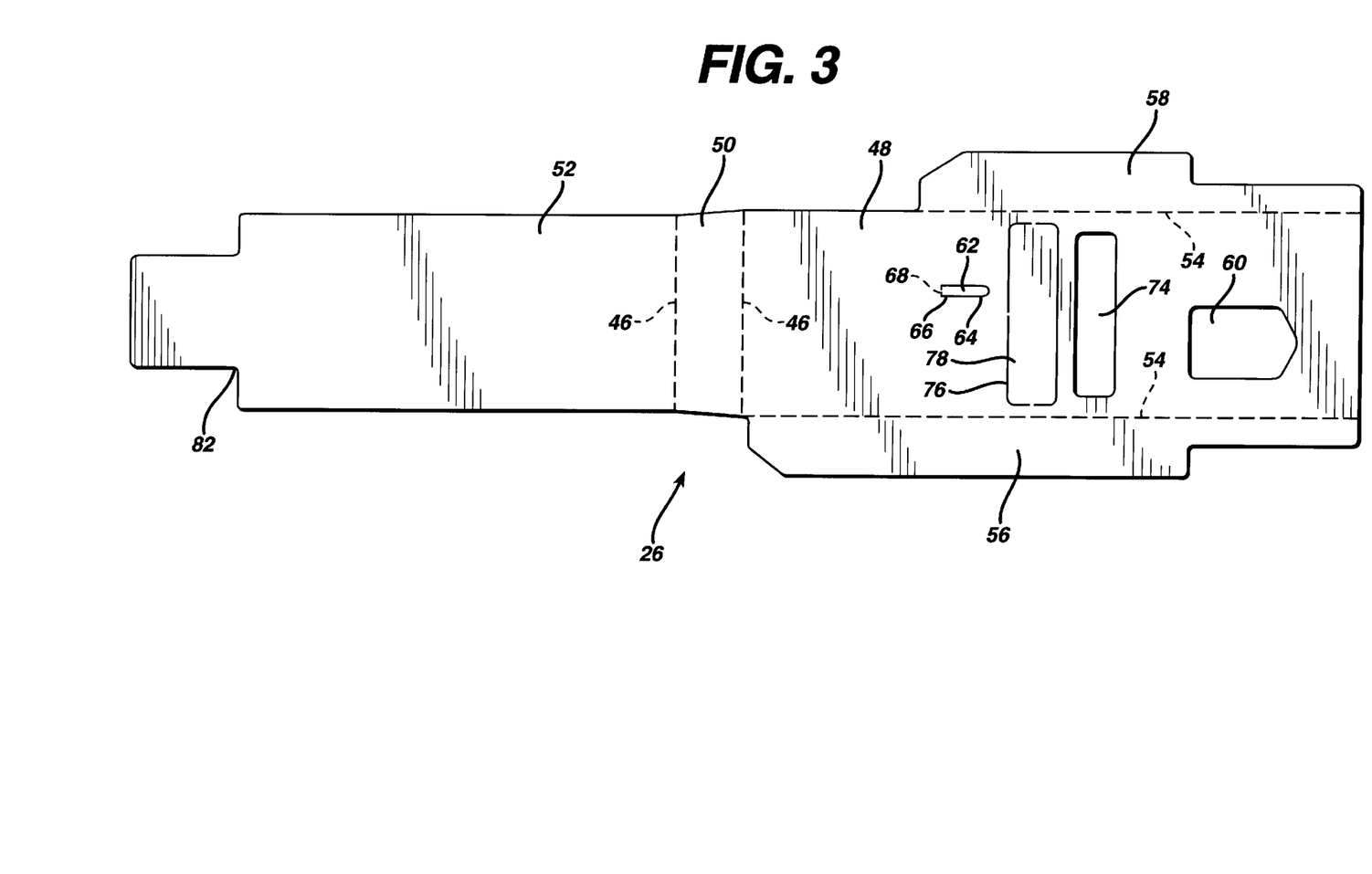
FIG. 3 is a plan view of an unfolded blank forming an inner layer of the sleeve of FIG. 1.

Returning to FIG. 2, the sleeve inner layer 26 wraps about the cassette 24. Thus, if any small droplets of the hydrogen peroxide solution are left on the outside of the cassette 24 after use, they will be absorbed by the cardboard of the sleeve inner layer 26 thereby preventing contact with an operator's hands or clothing. The sleeve inner layer 26 provides several other important functions as will become apparent. As is also seen in FIG. 3, the sleeve inner layer 26 folds about a pair of parallel fold lines 46 to form an upper panel 48, an end panel 50, and a lower panel 52. A pair of longitudinal fold lines 54 forms a first side panel 56 and second side panel 58. A large arrow shaped aperture 60 in the upper panel 48 points toward the sleeve open end 23. Also, a tab 62 comprises a small longitudinally elongate cutout that remains attached at its rearward end 66 (toward the sleeve closed end) thereby forming a fold line 68 about which the tab 62 rotates through 180°.

Figure 6:
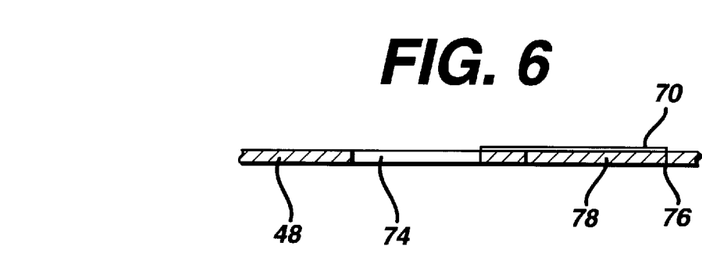
FIG. 6 is a sectional view of the label of FIG. 5 shown in the retracted position.
Figure 7:
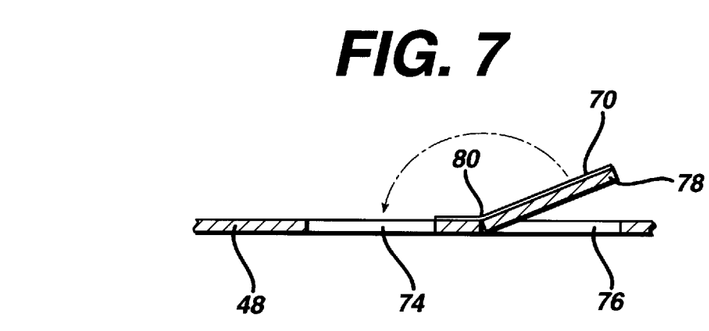
FIG. 7 is a sectional view as in FIG. 6, showing the label in a transitional orientation.
Figure 8:
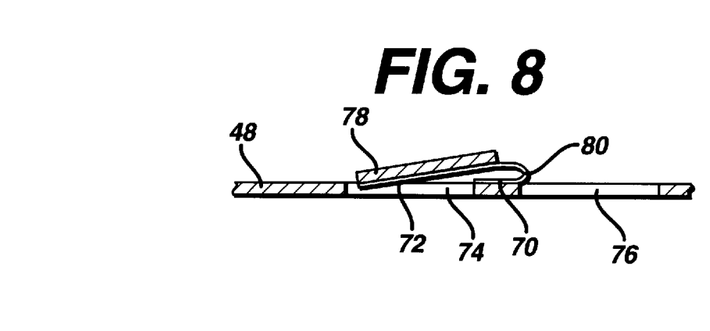
FIG. 8 is a sectional view as in FIG. 6, showing the label in the exposed orientation wherein the label is viewable through an aperture.

A label 70, preferably with computer readable indicia 72 such as a bar code, identifies the cassette assembly 20. A large lateral rectangular aperture 74 form a window through which the label 70 becomes visible A tangular cutout 76 sits immediately rearward of the window are 74 and forms a removable panel 78 of cardboard, which fits within the cutout 76. The label 70 has adhesive on its surface opposite the indicia 72 and attaches to the removable panel 78 and to the inner sleeve upper panel 48 between the cutout 76 and window aperture 74. As shown in FIGS. 5 to 8, this forms a hinge 80 which allows the label to rotate through 180° from a position as shown in FIG. 6 wherein the removable panel 78 is received within the cutout 76 and the label indicia 72 are not visible through the window aperture 74, through the position shown in FIG. 7, to the position shown in FIG. 8 wherein the label indicia 72 becomes visible through the window apreture 74.

Returning to FIG. 2, cutouts 82 at the lateral side edges of the inner sleeve upper panel 48 near the sleeve open end 23, and additional cutouts 84 aligned therewith in the inner sleeve first and second side panels 56 and 58, provide access to the cassette 24 through the sleeve inner layer 26. Similar cutouts 86 are provided in the sleeve outer layer 28 in registry with the cutouts 82 and 84 to provide access to the cassette 24 through the entire sleeve 22.

Figure 4:
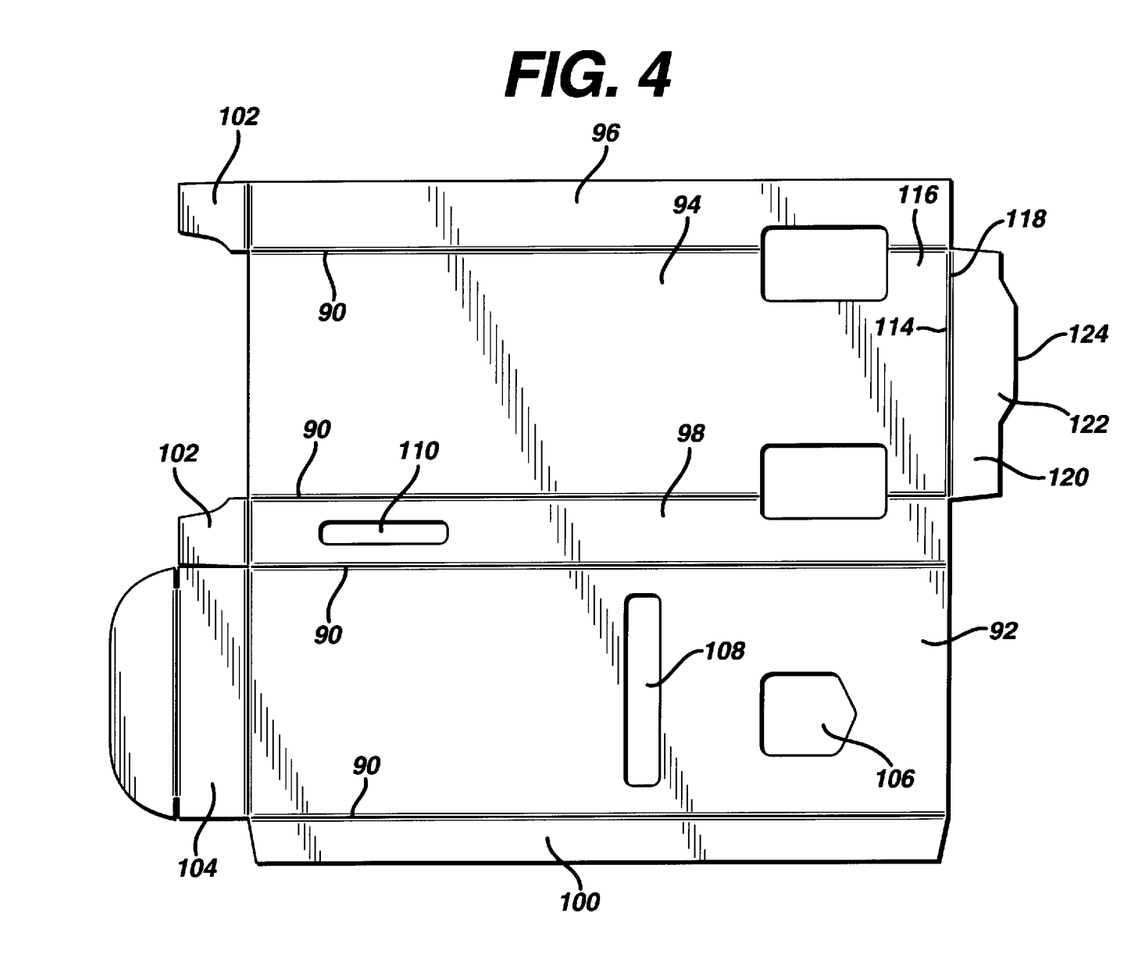
FIG. 4 is a plan view of an unfolded blank of an outer layer of the sleeve of FIG. 1.
Figure 5:
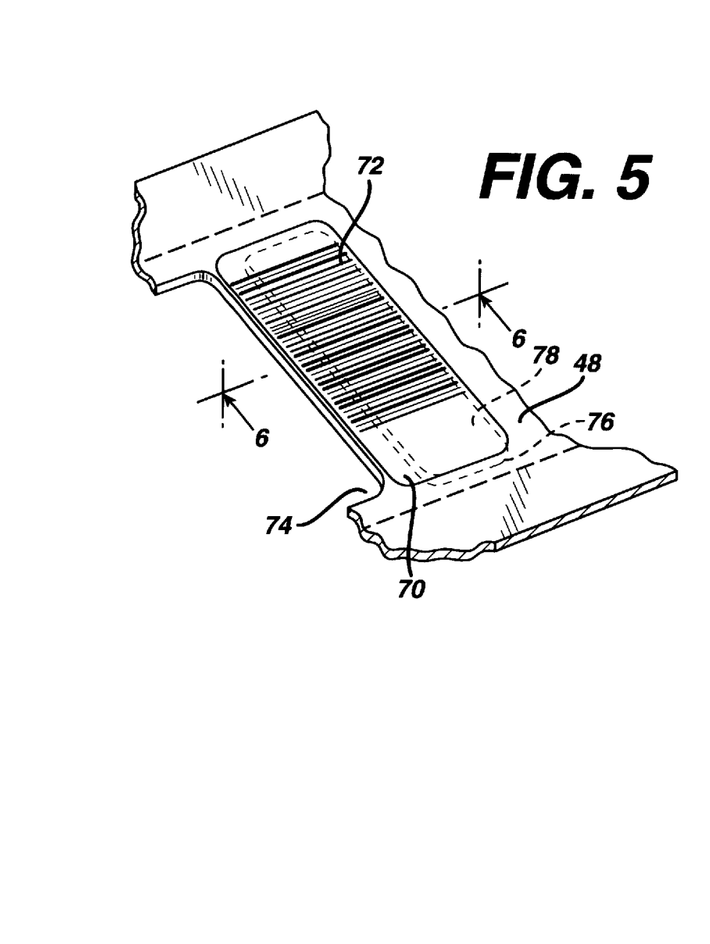
FIG. 5 is a perspective view of an identifying label according to the present invention on the sleeve inner layer of FIG. 3.

FIGS. 2 and 4 best illustrate the structure of the sleeve outer layer 28. It is formed of folded pressboard stock, but of course could be formed of other folded stock material such as a suitable polymer, or could be molded or formed in some other fashion to form an equivalent structure to that disclosed here. Longitudinal fold lines 90 form a top panel 92, bottom panel 94, a first side panel 96 and a second side panel 98, which correspond to the sleeve inner layer 26, upper panel 48, lower pan 52, first side panel 56 and second side panel 58. The longitudinal fold lies 90 also form a glue flap 100 which seals to the first side panel 96 to form the three dimensional structure of the outer sleeve layer 28. Side tabs 102 and a foldable flap 104 form the closed end 25 of the sleeve outer layer 28. Of course, other closure means such as glue flaps may be substituted therefor. An arrow shaped aperture 106 and a rectangular window 108 in the top panel 92 register with the corresponding openings 60 and 74 in the sleeve inner layer 26. The rectangular window 110 in the second side panel 98 provides viewing for indicia 112 on the cassette 24.

A lateral fold line 114 at the forward end 116 of the bottom panel 94 forms a hinge 118 about which rotates a retaining flap 120. The retaining flap 120 extends from the fold line 114 to terminate in a tang 122; a terminal edge 124 of which engages the cassette 24 to retain the cassette 24 within the sleeve 22. An annular post 126 surrounds each of the piercing apertures 44 in the cassette 24 such that the aperture 44 extends axially through the post 126. The post has a vertical annular sidewall 128 against which the terminal edge 124 abuts. The retaining flap 120 performs a surprisingly good job of holding the cassette 24 within the sleeve 22. Even fairly vigorous shaking will not dislodge the cassette 24 from the sleeve 22.

A fresh cassette assembly 20 having its cells 32 filled with hydrogen peroxide is configured as follows: the cassette 24 is received within the sleeve inner layer 26. The label 70 is folded into the position shown in FIG. 8 wherein the label indicia 72 are visible through the window apertures 74 and 108. Also, the tab 62 is folded over 180° to face rewardly. The cells 32 are received within chambers within the cassette shell 30, the outer surface 132 of which is rounded. The tab 62 engages this rounded outer surface 132 to provide a certain degree of resistance to movement between the cassette 24 and the sleeve 22. The sleeve inner layer 26 is received within the sleeve outer layer 28 with the retaining flap 120 folded over the inner layer 26 and into the sleeve 22 where its terminal edge 124 abuts the annular post vertical wall 128 on the cassette 24 thereby retaining the sleeve inner layer 26 and the cassette 24 within the sleeve outer layer 28.

Figure 9:
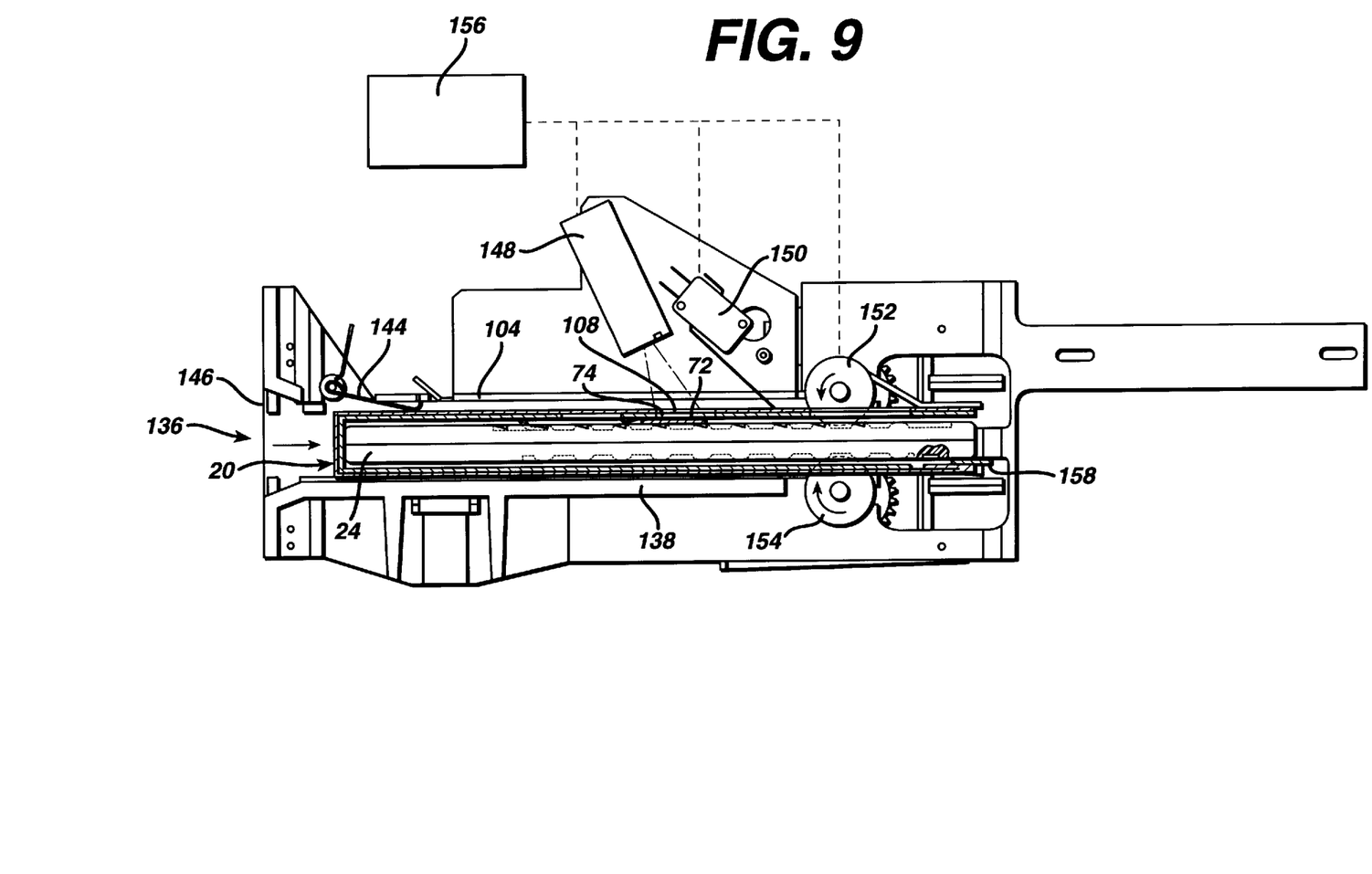
FIG. 9 is a cut-away view of the cassette and sleeve of FIG. 1 positioned within a cassette handling mechanism and showing the cassette upon entry into the handling system.

The cassette assembly 20 is intended for use with an automatic cassette extraction mechanism 134 as is shown in FIGS. 9 to 15. Turning to FIG. 9, the extraction mechanism 134 comprises a receiving slot 136 sized to receive the cassette assembly 20 with its sleeve open end 23 forward. The receiving slot 136 is outlined by a lower wall 138, an upper wall and two opposing sidewalls 142 (see also FIG. 15). A spring-loaded door 144 at an entrance 146 to the receiving 136 closes the receiving slot 136 when not in use and provides a downward biasing force against the cassette 24 to hold it firmly against the lower wall 138.

A bar code reader 148 is positioned above the lower wall 138 in such a fashion as to read the label indicia 72 as the cassette 24 is inserted into the receiving slot 136. A pressure switch senses the presence of a cassette 24 within the receiving slot 136. position sensing switch 150 engages the bar-code reader 148, and also engages an upper drive wheel 152 and a pair of lower drive wheels 154. If the bar code reader 148 fails to read the presence of a valid bar code label 70, then the drive wheels 152 and 154 will reverse to eject the cassette assembly 20 from the receiving slot 136. Assuming that the bar code reader 148 successfully reads the label 70, the label information, including lot code and shelf life data, will be fed to a control unit 156 for use in the sterilization control process. The control unit 156 is also operably connected to the position sensing switch 150 and the drive wheels 152 and 154 to control the label reading and cassette extraction process. Any suitable control unit may be employed, such as a microprocessor based automatic control system, and multiple controllers may be used for controlling various aspects of the operation described herein.

Figure 15:
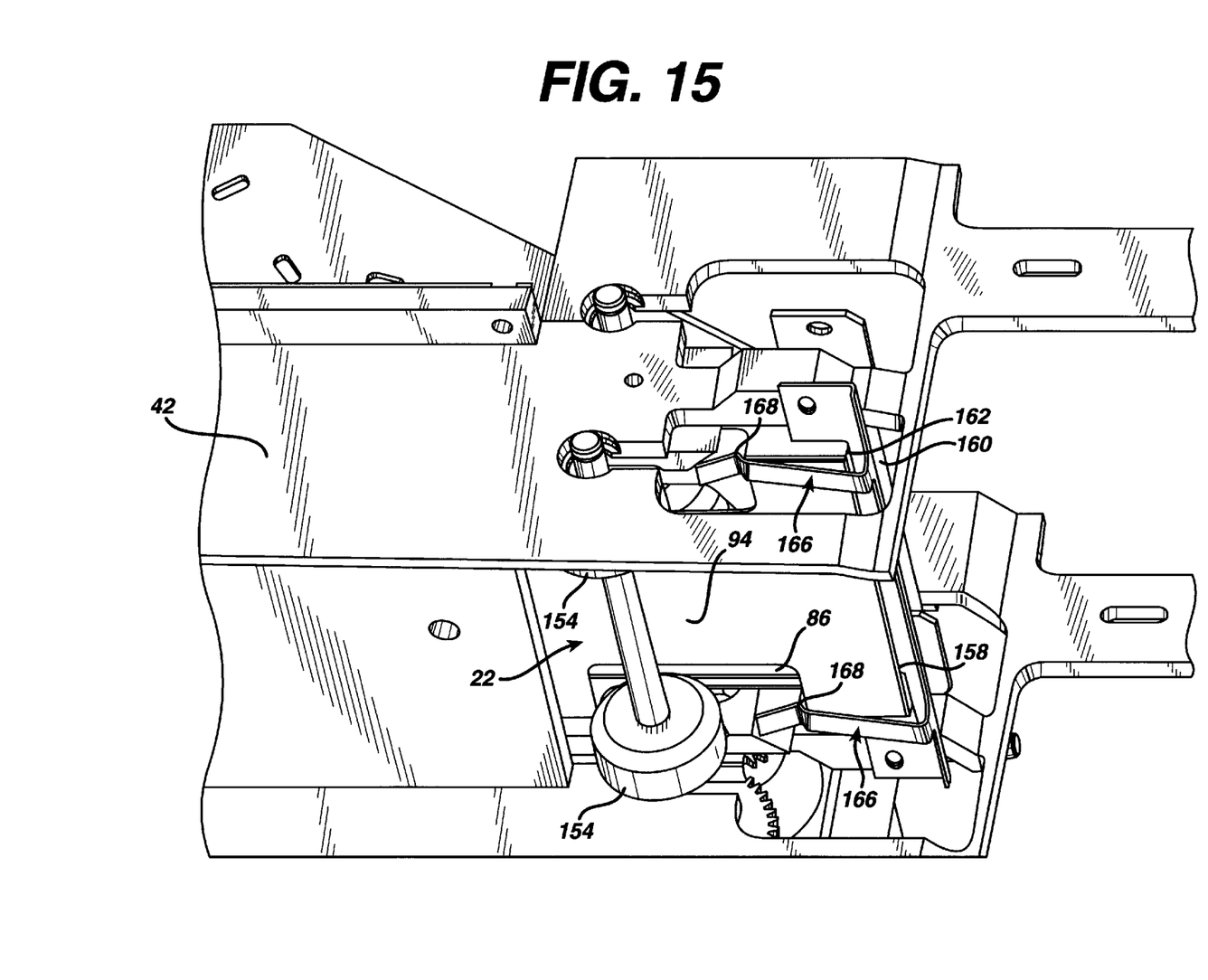
FIG. 15 is a front and bottom cut-away perspective view of the cassette handling system.

As is best seen in FIGS. 9 and 15, as the cassette assembly 20 is received into the receiving slot 136, a projection or opener 158 on the loading mechanism 134 slides between the cassette 24 and retaining flap 120 to rotate the retaining flap downwardly and out of engagement with the cassette 24. This allows the cassette 24 to slide outwardly of the sleeve 22. The opener 158 extends laterally from a bracket 160 and an edge 162 on the bracket 160 adjacent the opener 158 abuts forward edges 164 of the sleeve 22 to limit forward movement of the sleeve 22. A pair of spring clips 166 project laterally and slightly upwardly from the bracket 160. Each of the spring clips 166 has a upwardly extending lip 168 thereon which slides into the cut outs 82 and 86 of the sleeve inner layer 26 and outer layer 28, respectively, to hold the sleeve 22 firmly in position. With the cassette assembly 22 in this position, the lower drive wheels 154 also protrude through the cut outs 82 and 86 to engage the cassette lower housing 36, and the upper drive wheel 152 protrudes through the arrow shaped apertures 60 and 106 to engage the cassette upper housing 34. Thus, rotation of the drive wheels urges the cassette 24 outwardly of the sleeve 22 through its open end 23.

Resistance to movement between the cassette 24 and sleeve 22 provided by the tab 62 ensures that if the cassette assembly 20 is not already properly positioned against the bracket edge 162, the sleeve 22 will move forwardly with the cassette 24 until the sleeve 22 is properly in position. At this point, the resistance provided by the tab 62 can no longer restrain movement of the cassette 24 and it will move forwardly out of the sleeve 22.

Figure 10:
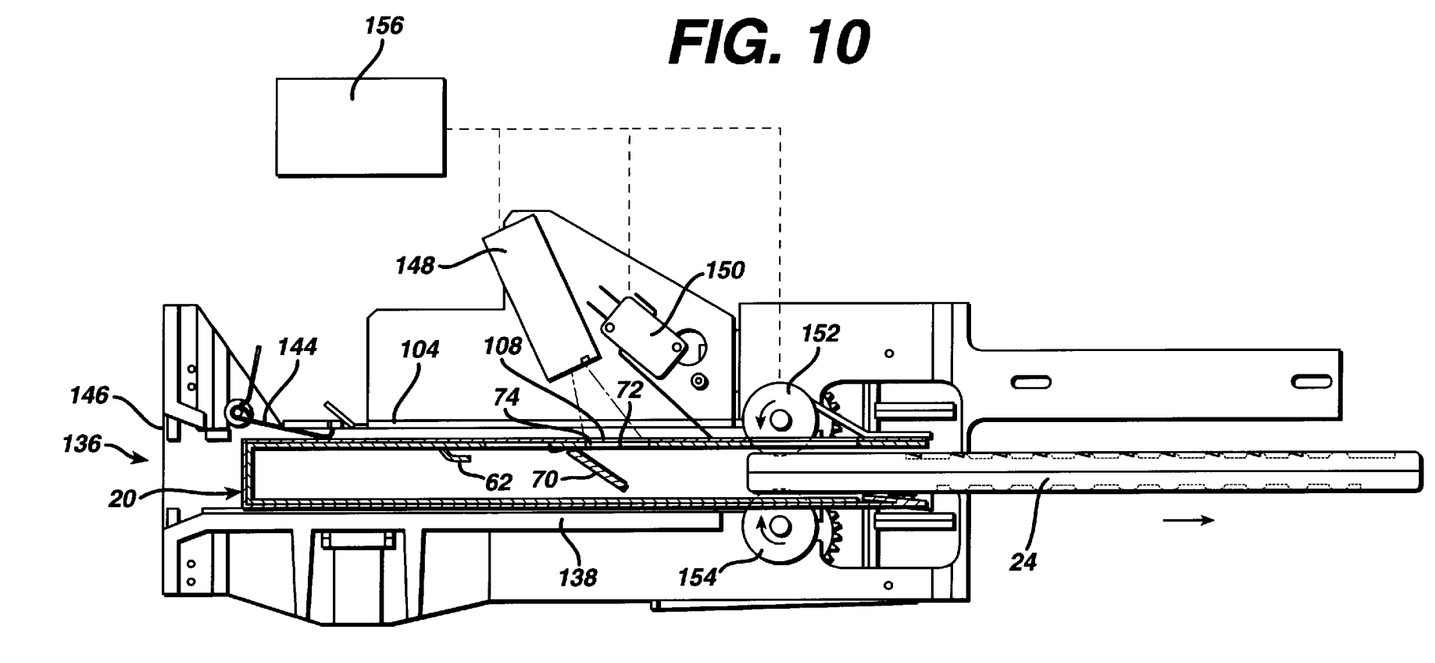
FIG. 10 is a view of the cassette, sleeve and handling system in accordance with FIG. 9 and showing the cassette traveling out of the sleeve.
Figure 16:
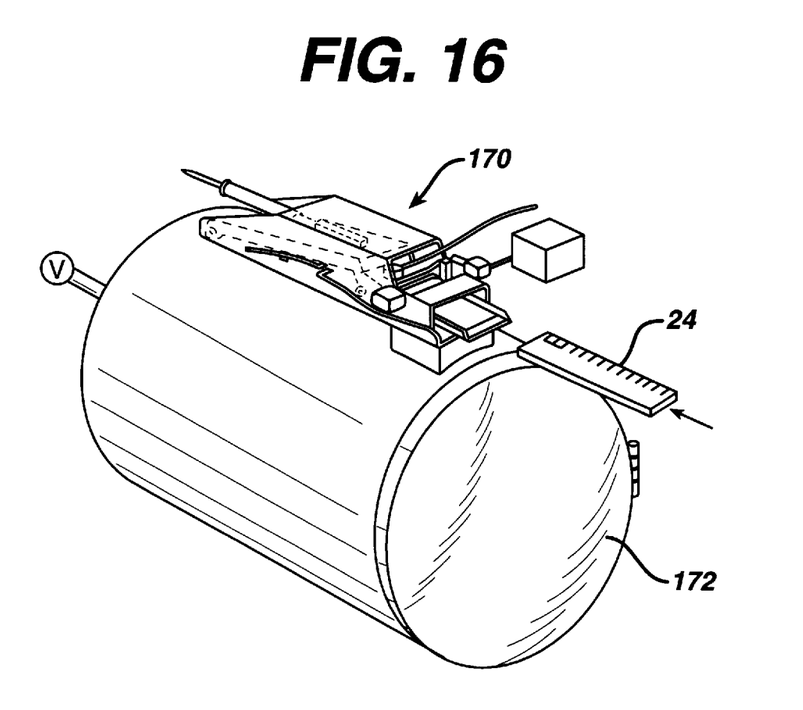
FIG. 16 perspective view of a sterilizing chamber and fluid extraction mechanism.

Turning to FIG. 10, as the cassette 24 moves out of the sleeve 22, the springiness of the label 70 and the weight of the removable panel 78 urge the label 70 to hang downwardly about its hinge point 80. The cassette 24 then moves out of the extraction mechanism 134 and into a fluid handling system 170 such as is shown in FIG. 16, with the cassette extracts mechanism 134 removed for clarity. The fluid handling system 170 extracts the measured quantity of hydrogen peroxide from a cell 32 through the needle 42 (see FIG. 2A) to deliver it to a sterilization chamber 172 to sterile articles (not shown) contained therein. Operation of this mechanism is more fully described in the Wlliams et al. U.S. Pat. Nos. 4,817,800 issued Apr. 4, 1989; 4,913,196 issued Apr. 3, 1990; 4,938,262 issued Jul. 3, 1990; and 4,941,518 issued Jul. 17, 1990, all of which are incorporated herein by reference.

Figure 11:
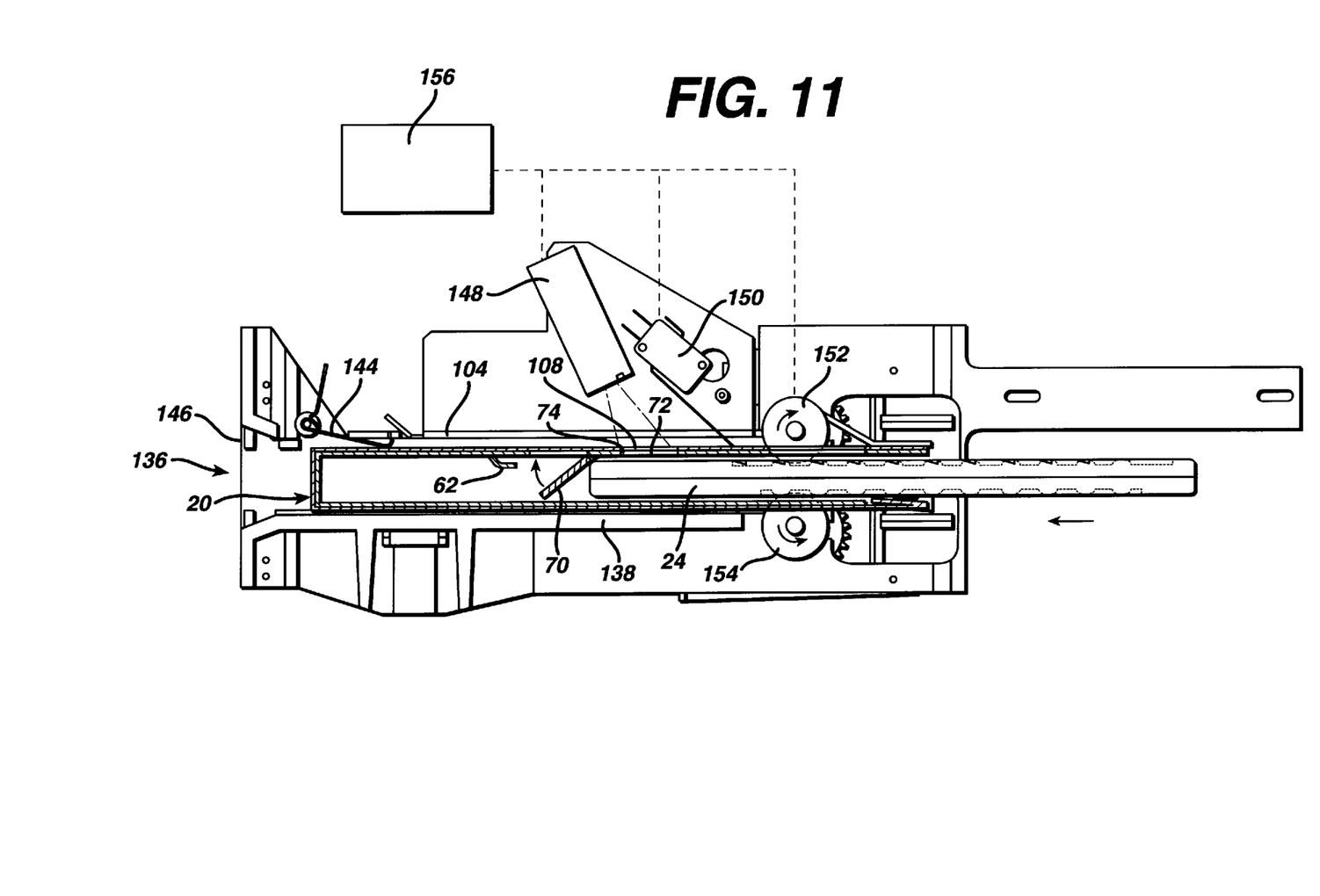
FIG. 11 is a view of the cassette, sleeve and handling system in accordance with FIG. 9 and showing the traveling back into the sleeve.
Figure 12:
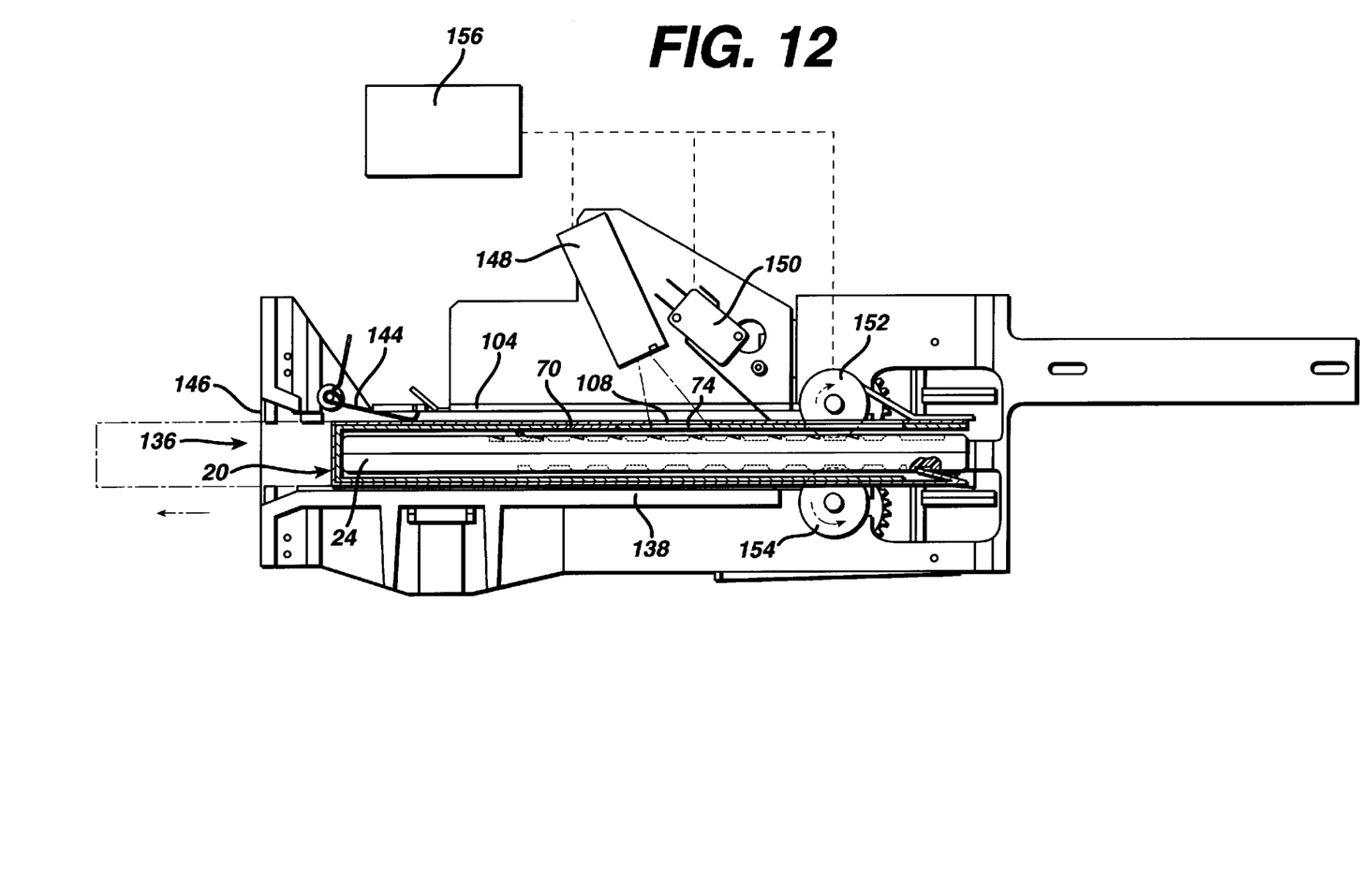
FIG. 12 is a view of the cassette, sleeve and handling system in accordance with FIG. 9 and showing the cassette repositioned within the sleeve in preparation for leaving the handling system.
Figure 13:
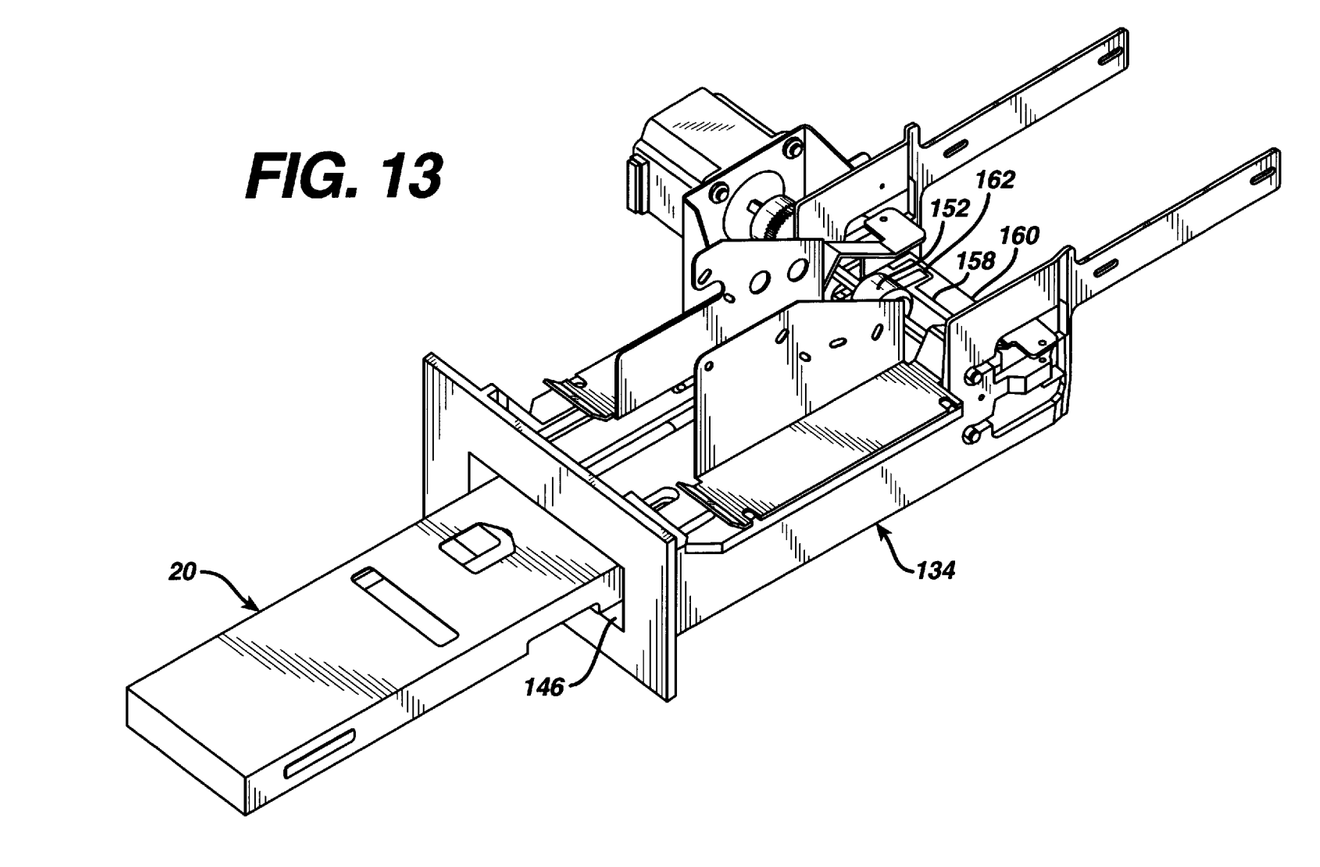
FIG. 13 is a cut-away perspective view of the cassette and sleeve assembly entering the cassette handling assembly.
Figure 14:
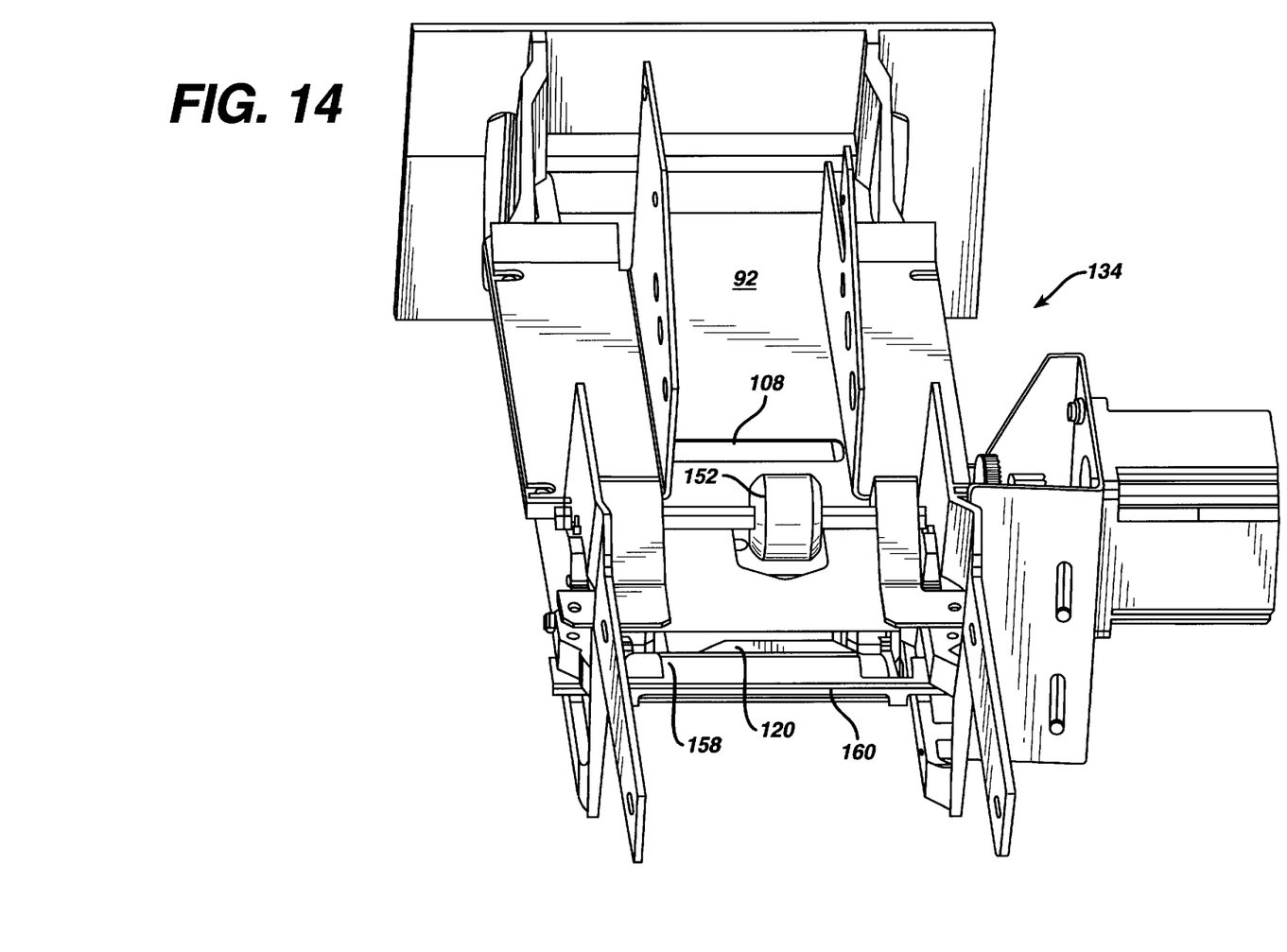
FIG. 14 is a front and-top cut-away perspective view of the cassette handling system.

When spent, the cassette 24 returns from the fluid handling system 170 and the drive wheels 152 and 154 push it home into the sleeve 22, as shown in FIG. 11. As the cassette 24 moves into the sleeve 22, its rearward end contacts the label 70 causing it to rotate backwards to the position illustrated in FIG. 6 wherein the label indicia 72 are not visible exterior of the sleeve 22. Turning to FIG. 12, the cassette assembly 20 then moves outwardly of the receiving slot 136. The opener 158 slides out of the sleeve 22 thus allowing the retaining flap 120 to move upwardly into engagement with the cassette 24. The cassette assembly 20 is thus ejected from the receiving slot 136 with the cassette 24 firmly received with the sleeve 22.

Any drops of hydrogen peroxide solution which may remain on the outside of the cassette, although unlikely, would nevertheless be absorbed and retained by the sleeve inner layer 26 thereby protecting an operator therefrom. If the spent cassette is reinserted in to the receiving slot 136, the indicia 72 on the label 70 will not be visible due to the folding over of the label 70 during the cassette reinsertion. When the bar code reader 148 senses the lack of identifying indicia 72, the control unit 156 instructs the drive wheels 152 and 154 to immediately eject the cassette assembly 20. Of course, other actions can result in rejection of the cassette assembly 20. For instance, the control unit could be programmed to reject the cassette assembly if the bar code data indicates that the cassette assembly 20 has exceeded its shelf life, or if the lot code has previously been identified as rejected.

While the invention has been described with regard to a particular embodiment thereof, those skilled in the art will understand, of course, that the invention is not limited thereto since modifications can be made by those skilled in the art, particularly in light of the foregoing teachings. Reasonable variation and modification are possible within the foregoing disclosure of the invention without the departing from the spirit of the invention.

For example, the novel cassette assembly and handling techniques may be applied to other processes outside of sterilization. The techniques described herein have utility for handling a variety of cassettes, such as for example, cassettes containing reagents for chemical or medical tests. The contents of the cassette need not be liquid and the invention is not limited to any specific material or method of extracting such material from the cassette.

Further, other structures than presented herein may accomplish the teachings of the present invention. The retaining flap 120 need not face inwardly of the sleeve 22 to abut a surface on a face of the cassette. Instead, it could abut an end of the cassette, or could abut a surface on the sleeve, such as a folded-in lip on the edge of the sleeve opposite the flap 120 at the cassette open end. In this case, the spring in the material of the sleeve would hold the flap 120 in place.

Other means of providing resistance to movement between the cassette 20 and the sleeve 22 could substitute for the tab 62. For instance, rearwardly facing projections could be formed on the sleeve, or attached thereto.

While the adhesive label 70 in combination with the mass of the cut-out portion 78 disclosed above provides a convenient expedient for placing indicia 72 on the cassette assembly 20, other configurations may be substituted therefor. For example, the cut-out portion 78 stiffens the label 70, but other known means of providing a stiff label may be substituted therefor. The label may be formed of stiff stock in which case adhesive need only be applied at the attachment to the sleeve, other stiffening material could be attached thereto, and depending upon the materials of construction, the label may be attached by alternative means to adhesive. Alternatively, the cut-out portion 78 may be cut to form a natural hinge, as by cutting only three instead of four sides and the indicia may be printed directly onto the cut-out portion 78. Many expedients to providing a movable label will be appreciated by those of skill in the art upon examination of this specification.

Various modifications and alterations of this invention will be apparent to those skilled in the art without departing from the scope and spirit of this invention. It should be understood that the invention is not limited to the embodiments disclosed herein, and that the claims should be interpreted as broadly as the prior art allows.

What is claimed is:

1. A cassette assembly comprising:

a cassette having a first side and a first end;

a protective sleeve containing the cassette, the sleeve comprising a first side and a first end, the first side having a window aperture therethrough; and a label member within the sleeve having indicia thereon, the label member being rotatably mounted about a first hinge adjacent the window aperture, the label member having:

a first position of rotation about the first hinge with the cassette within the sleeve wherein the label indicia is in registry with said window aperture whereby the label indicia is visible therethrough, and a second position of rotation about the first hinge with the cassette within the sleeve wherein the label indicia is out of registry with said window whereby the label indicia is not visible through the window aperture; and the first hinge being oriented with respect to the sleeve first end so that when the cassette is inserted through the first end, the cassette abuts the label member and urges it about the hinge into the second position, whereby extraction of the cassette from the sleeve and reinsertion of the cassette into the sleeve moves the label member from the first position to the second position to indicate that the cassette has been at least once extracted from the sleeve.

2. The cassette assembly according to claim 1 wherein the label member further comprises a biasing means to bias the label member away from the first position when the cassette is not received within the sleeve.

3. The cassette assembly according to claim 2 wherein the biasing means comprises an elastic member which urges the label member away from the first position.

4. The cassette assembly according to claim 2 wherein the biasing means comprises the label member having a mass and the sleeve being oriented so that gravity urges the mass of the label member away from the first position.

5. The cassette assembly according to claim 2 wherein the label member comprises an adhesive label adhered to the sleeve adjacent the window aperture and the first hinge comprises a fold line on the adhesive label.

6. The cassette assembly according to claim 5 wherein the sleeve is formed of stock and further comprises a cut-out adjacent the viewing window which forms a removable panel of the stock, the adhesive label being attached thereto whereby the panel stiffens the label and defines the fold line thereon.

7. The cassette assembly according to claim 6 and further comprising a retaining member connected to the sleeve by a second hinge at the sleeve first end, the retaining member being rotatable about the second hinge from a first position in which the retaining member blocks the travel of the cassette out of the sleeve through the sleeve first end; and a second position in which the retaining member does not block travel of the cassette out of the sleeve through the sleeve first end.

8. A cassette assembly according to claim 7 wherein the sleeve is formed of foldable stock, the retaining member comprises a flap, the second hinge comprises a first fold line in the stock and the biasing means comprises the tendency for the stock to unfold along the first fold line in the stock.

9. A cassette assembly according to claim 6 wherein the retaining member extends from the second hinge, between the sleeve and the cassette, to a terminal edge which abuts a surface on the cassette when the retaining member is in its first position to block travel of the cassette out of the sleeve through the sleeve first end.

10. A cassette assembly according to claim 9 wherein the sleeve is formed of foldable stock, the retaining member comprises a flap, the second hinge comprises a first fold line in the stock and the biasing means comprises the tendency for the stock to unfold along the first fold line.

11. The cassette assembly according to claim 1 and further comprising a retaining member connected to the sleeve by a second hinge at the sleeve first end, the retaining member being rotatable about the second hinge from a first position in which the retaining member blocks the travel of the cassette out of the sleeve through the sleeve first end; and a second position in which the retaining member does not block travel of the cassette out of the sleeve through the sleeve first end.

12. A cassette assembly according to claim 11 wherein the retaining member extends from the second hinge, between the sleeve and the cassette, to a terminal edge which abuts a surface on the cassette when the retaining member is in its first position to block travel of the cassette out of the sleeve through the sleeve first end.

13. A method for delivering a cassette to a device comprising the steps of:

placing the cassette within a protective sleeve having an open end;

hingably mounting a label member with an indicia thereon within the sleeve;

rotating the label member into a first position with the indicia visible through a window aperture through the sleeve;

abutting the label member with the cassette when the cassette is within the sleeve to hold the label member in the first position;

sliding the cassette out of the sleeve through its open end;

processing the cassette in the device; and sliding the cassette back into the sleeve through its open end and abutting the label member thereby to swing the label member to a second position with the indicia out of register with the window aperture and not visible therethrough.

14. A method according to claim 13 wherein the step of processing the cassette comprises removing a substance from the cassette.

15. A method according to claim 13 wherein the steps of sliding the cassette out of and back into the sleeve through its open end are performed by a machine.

16. A method according to claim 15 and further comprising the steps of reading the label indicia with a sensor prior to the step of processing the cassette in the device.

17. A method according to claim 16 and wherein the steps of reading the label indicia, sliding the cassette out of the sleeve, processing the cassette and sliding the cassette back into the sleeve are controlled by an automatic control unit.

18. A method according to clam 17 wherein the automatic control unit is programmed to not perform the steps of processing the cassette if the sensor fails to first read the presence of the label indicia.

19. A method according to clam 17 wherein the automatic control unit is programmed to not perform the steps of processing the cassette if the label indicia indicates that the cassette is not proper.

20. A method according to claim 19 wherein when the indicia indicates that the cassette has improper contents for processing the cassette is deemed not proper.

21. A method according to claim 19 wherein when the indicia indicates that the cassette is beyond an expiration date the cassette is deemed not proper.

22. A method according to claim 13 further comprising the steps of:

folding a flap on the sleeve inwardly of the sleeve open end to abut a retaining surface on the cassette and block travel of the cassette outwardly of the sleeve through the sleeve open end; and inserting an opening member into the cassette open end to abut the flap and move the flap out of engagement with the retaining surface.

* * * * *